United States Patent [19]

Phillips et al.

[11] 3,969,407

[45] July 13, 1976

[54] SUBSTITUTED CARBAMOYL SULFINES AND THEIR MANUFACTURE

[75] Inventors: Wendell Gary Phillips, Olivette; Kenneth Wayne Ratts, Creve Coeur, both of Mo.

[73] Assignee: Monsanto Company, St. Louis, Mo.

[22] Filed: Nov. 1, 1971

[21] Appl. No.: 194,539

[52] U.S. Cl.................. 260/561 S; 260/239 B; 260/326.82; 260/465 D; 260/543 R; 260/562 S
[51] Int. Cl.².............. C07C 103/12; C07C 103/34
[58] Field of Search......... 260/543 H, 543 R, 561 S, 260/562

[56] References Cited

UNITED STATES PATENTS 3,770,824   11/1973   Phillips .................... 260/543 H

*Primary Examiner*—Norman Morgenstern
*Attorney, Agent, or Firm*—William I. Andress

[57] ABSTRACT

Substituted carbamoyl sulfines are prepared from dichloromethane sulfenyl chlorides by reaction with an aqueous base or by oxidation of thioformyl chlorides by a peracid. The compounds of this invention are pesticidally active and particularly useful as selective herbicides.

30 Claims, No Drawings

SUBSTITUTED CARBAMOYL SULFINES AND THEIR MANUFACTURE

This invention relates to substituted carbamoyl sulfines of the formula

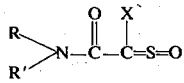

wherein R and R' are each independently selected from hydrogen, lower alkyl, alkoxyalkyl of from 2 through 8 carbons, benzyl, phenyl, substituted phenyl wherein the ring substituents thereof total from 1 through 3 same or different substituents selected from the group of substituents consisting of lower alkyl, lower alkoxy, halo, nitro, cyano and trihalomethyl, provided that the number of nitro substituents be from 0 through 2, and substituted benzyl wherein the substituents are on the phenyl ring and are as defined for substituted phenyl, or R and R' when taken together are alkylene of the empirical formula $C_nH_{2n}$ wherein $n$ is an integer from 4 through 8, inclusive, and having from 4 through 8 carbons in a continuous chain between the nitrogen terminal valence bonds and X is chloro or lower alkyl provided that when X is lower alkyl, R' is hydrogen.

Lower alkyl have from 1 through 5 carbons, inclusive. Examples of lower alkyl include methyl, ethyl, propyl, butyl, pentyl and the various isomeric forms thereof.

Lower alkoxy have from 1 through 5 carbons, inclusive. Examples of alkoxy include methoxy, ethoxy, propoxy, butoxy, pentoxy and the various isomeric forms thereof.

Halo is a halogen selected from the group consisting of fluorine, chlorine, bromine and iodine.

Examples of alkoxyalkyl of from 2 through 8 carbons include, but are not limited to, propoxymethyl, butoxybutyl, butoxyethyl, methoxymethyl, and ethoxypropyl.

Examples of heterocyclic groups of nitrogen and alkylene of the empirical formula $C_nH_{2n}$ wherein $n$ is an integer from 4 through 8, inclusive, and having from 4 through 8 carbons in a continuous chain between the nitrogen terminal valence bonds include, but are not limited to, pyrrolidinyl, piperidinyl, hexamethyleneimino, heptamethyleneimino, octamethyleneimino, 2-ethylpyrrolidinyl, 3-butylpyrrolidinyl, 2,5-dimethylpyrrolidinyl, 2,5-diethylpyrrolidinyl, 3,4-dimethylpyrrolidinyl, 2-pipecolinyl, 3-pipecolinyl, 4-pipecolinyl, 2,6-dimethylpiperidinyl, 2-ethyl-6-methylpiperidinyl, 2-propylpiperidinyl, 3-methylhexamethyleneimino, 3,4-dimetylhexamethyleneimino, and the various isomeric forms thereof.

Compounds of this invention having the formula

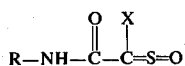

are conveniently and efficiently prepared by the reaction of about one molecular proportion of a chloromethane sulfenyl chloride of the formula

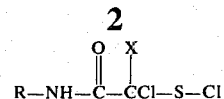

wherein R and X have the aforementioned significance and about two equivalent proportions of an aqueous base. Examples of bases useful in this method of preparation include, but are not limited to, sodium bicarbonate, sodium carbonate, alkali metal carbonates and bicarbonates, and dilute solutions of alkali metal hydroxides, i.e. about 0.1 molar solution or less. Although the reaction proceeds more slowly, water by itself can be the aqueous base. Sodium bicarbonate is a preferred aqueous base. When the reaction mass is a two-phase system, agitation during the reaction is reaction to keep the aqueous base in intimate contact with the organic phase containing the sulfenyl chloride and the desired reaction product. When an organic solvent is used, which is miscible with water, agitation of the system is preferred but not necessary. The aqueous base may be present in excess of twice the equivalent amount of the sulfenyl chloride. Preferably, the amount of aqueous base ranges from about two times to about ten times the equivalent amount of the sulfenyl chloride. The amount of water in which the aqueous base is dissolved is generally at least sufficient to provide a saturated solution of the base when the base is a carbonate or a bicarbonate or sufficient to provide a 0.1 molar solution when the base is an alkali metal hydroxide. When an organic solvent is present in the reaction mass the amount of water is usually substantially equivalent in volume to the volume of organic solvent. Greater or lesser amounts of water may be used depending on various reaction considerations. It is more preferred that the amount of water be from about 1/8th the volume of organic solvent to about 5 times the volume of organic solvent, and, still more preferred, from about 1/4th to about twice the volume of organic solvent.

The reaction mass may consist only of the aforedescribed reactants and their reaction products or it may contain other components in addition such as diluents, other inert materials and solvents, i.e., common organic liquids which are inert under the reaction conditions and which may dissolve one or more of the reactants or products of the reaction, which solvents are exemplified by but not limited to aliphatic hydrocarbons, such as pentane, hexane, mineral spirits, etc., aromatics such as benzene, toluene, xylenes, etc., ethers such as diethyl ether, diisopropyl ether, petroleum ether, etc., esters such as methyl acetate, ethyl acetate, propyl acetate, etc., and other organics such as tetrahydrofuran, etc. The chloride salt by-products is generally not soluble in the above organic solvents but is soluble in water. When the organic solvent is not miscible with water or when the system contains no organic solvent, the salt may be readily removed from the reaction mass by removal of the aqueous layer.

The reaction is normally carried out at a temperature above the freezing point of the system but preferably not above 50° Centigrade. Although the reaction may be conducted above 50°C., the yield of by-products from side reactions which form at increased temperatures becomes so great that yield of product normally drops off rapidly with further temperature increases. Still more preferably, the reaction is carried out at temperatures of from about 0°C. to about 30°C. The reaction is most conveniently carried out at room temperature, about 23°C., in the presence of an organic solvent immiscible with water. The reaction is usually carried out at atmospheric pressure, but higher or lower pressures may be utilized if equipment and other factors favor such higher or lower pressures. The reaction may be carried out in an open vessel or under reflux.

Manufacture of chloromethane sulfenyl chlorides, used as starting materials in this method for the preparations of the compounds of the present invention, is taught in prior U.S. Pat. Applications Ser. No. 139,976 filed May 3, 1971, entitled "Substituted Alpha, Alpha-Dichloro-Methane Sulfenyl Chlorides and Their Manufacture" now U.S. Pat. No. 3,770,824 and Ser. No. 139,977 filed May 3, 1971, entitled "Substituted Alpha-Chloro-Methane-Sulfenyl Chlorides and Their Manufacture" now U.S. Pat. No. 3,803,224.

The compounds of the present invention having the formula

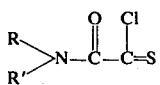

may also be prepared by the oxidation of a carbamoyl thioformyl chloride of the formula

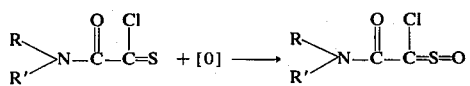

wherein R and R' have the aforementioned significance. The reaction is postulated to proceed as follows:

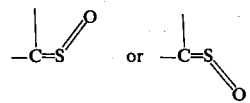

This method is particularly useful in the preparation of substituted 1-thiooxamoyl chloride, S-oxides of this invention when neither R nor R' is hydrogen.

The most convenient oxygen source for this oxidation is an organic peracid. An approximately equivalent amount of an organic peracid such as perbenzoic acid, perphthalic acid, halogenated perbenzoic acid and the like, supplies sufficient oxygen to form the desired compound of this invention in good yield without excessive tar or by-product formation. Improved yields are obtained when the quantity of organic peracid is slightly less than the equivalent amount. In a preferred embodiment the amount of organic peracid is about 9/10 of the equivalent amount.

The reaction mass may consist only of the aforedescribed reactants and their reaction products or it may contain other components in addition such as diluents, other inert materials and solvents as described hereinbefore.

The reaction is normally carried out at a temperature above the freezing point of the system but preferably not above the boiling point of the system. The reaction is most conveniently carried out at room temperature, about 23°C., in the presence of an organic solvent. The reaction is usually carried out at atmospheric pressure, but higher or lower pressures may be utilized if equipment and other factors favor such higher or lower pressures. The reaction may be carried out in an open vessel or under reflux.

Manufacture of carbamoyl thioformyl chlorides, used as starting materials in this method for the preparation of the compounds of the present invention, is taught in prior U.S. Pat. Application Ser. No. 177,096 filed Aug. 24, 1971, entitled "Substituted Carbamoyl Thioformyl Chlorides and Their Manufacture" now U.S. Pat. No. 3,758,568.

For convenience, the structure of the compounds of this invention is written herein as

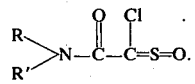

Although the structure of these compounds is not completely understood, it is postulated that

is not linear in configuration but rather is stereospecific having the configuration

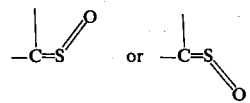

Each configuration may have a different melting point and may be considered a different chemical compound. When prepared by the methods described herein, the product may be a pure stereoisomer or a mixture of the two. It is further postulated that the isomers may be rearranged from one configuration to the other simply by mild heating, for example, by heating the compound for a brief period of time, about 30 to 60 minutes, on a steam bath. While the two isomers are believed to exist, it is not known in any particular instance whether the compound described is pure or a mixture of isomers. Thus, references, tests and descriptions herein may relate to either one of the pure isomers or a mixture of both.

Substituted carbamoyl sulfines of this invention are useful as biocides. Exemplary of such biocidal uses for these products is the control of nematodes, arachnids, arthropods and insects as well as eradication of noxious weeds. These compounds are particularly useful as pre-emergent and contact herbicides.

Pre-emergent and contact herbicidal compounds are useful in the selective killing of weeds in crops. In using the compounds of the present invention as pre-emergent and contact herbicides, the compounds can be used alone or in combination with a material referred to in the art as an adjuvant in liquid or solid form. Herbicidal fomulations are prepared by admixing the compound which is the active ingredient of the formulation with an adjuvant diluents, extenders, carriers and conditioning agents to provide compositions in the form of finely-divided particulate solids, granules, pellets, solutions, dispersions or emulsions. Thus, the active ingredient can be used with an adjuvant such as a finely-divided particulate solid, a liquid of organic origin, water, a wetting agent, dispersing agent, an emulsifying agent or any suitable combination of these. The herbicidal formulations usually contain from about 0.01 percent to about 99 percent by weight of the active ingredient. Application of these formulations to the soil or growth media can be carried out by simply admixing with the soil, by applying to the surface of the soil and thereafter dragging or discing into the soil to the desired depth, or by employing a liquid carrier to accomplish the penetration and impregnation. The application of liquid and particulate solid herbicidal formulations to the surface of soil or to above ground portions of plants can be carried out by conventional methods, e.g. power dusters, boom and hand sprayers and spray dusters. The formulations can also be applied from airplanes as a dust or a spray because of their effectiveness at low dosages. In further method, the distribution of the active ingredients in soil can be carried out by admixture with the water employed to irrigate the soil. In such procedures, the amount of water can be varied with the porosity and water holding capacity of the soil to obtain the desired depth of distribution of the active ingredients.

The exact amount of active ingredient to be employed is dependent upon the response desired in the plant as well as such other factors as the plant species and stage of development thereof, the specific soil and depth at which the active ingredients are distributed in the soil and the amount of rainfall as well as the specific active ingredient employed. In foliar treatment, the active ingredients are applied in amounts from about 1 to about 50 or more pounds per acre. In applications to soil for the control of the growth of germinant seeds, germinative seeds, emerging seedlings and established vegetation, the active ingredients are applied in amounts from about 0.1 to about 25 or more pounds per acre. It is believed that one skilled in the art can readily determine from the teachings of this specification the general procedure for any application.

As illustrative of this invention, but not limitative thereof, is the following:

EXAMPLE 1

To a suitable reaction vessel equipped with an agitator is charged approximately 100 milliliters (ml.) of dichloromethane. Approximately 8 grams (g.), about 0.026 moles, of 2,2,4'-trichloro-2-(chlorothio) acetanilide is added to and dissolved in the dichloromethane. Approximately 17 g., about 0.23 moles, of sodium bicarbonate is dissolved in about 100 ml. of water. This solution is then added. The mass is stirred for about 90 minutes. Thereafter the mass separates into two layers. The aqueous layer is removed using a separatory funnel. The remaining organic layer is dried over magnesium sulfate. The dichloromethane is then removed from the organic layer by vacuum distillation. The remaining tacky yellow solid is washed with diethyl ether and then is dissolved in and recrystallized from petroleum ether. The yellow solid is found to have a melting point of about 111° to 113°C. and is identified by nuclear magnetic resonance and elemental analysis as para-chloro-1-thiooxaniloyl chloride, S-oxide

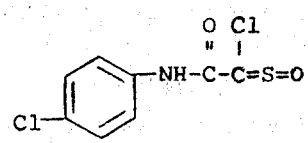

Calculated for $C_8H_5Cl_2NO_2S$: C, 38.42; H, 2.02; N, 5.60 Found: C, 38.65; H, 1.91; N, 5.52.

EXAMPLE 2

To a suitable reaction vessel equipped with an agitator is charged about 50 ml. of dichloromethane. Approximately 20 g., about 0.061 moles, of 2,2-dichloro-2-(chlorothio)meta-trifluoromethylacetanilide is added and dissolved in the dichloromethane. The solution becomes homogeneous. Approximately 11.5 g., about 0.137 moles, of sodium bicarbonate is dissolved in about 50 ml. of water. This solution is then added. The mass is stirred for about 1 hour at ambient room temperature, about 23°C. The mass is allowed to separate into two layers. The aqueous layer is removed in a separatory funnel. The remaining organic layer is dried over magnesium sulfate. The dichloromethane is removed from the organic layer by vacuum distillation leaving a residual oil. The oil is partially dissolved in 100 ml. of petroleum ether. Upon cooling to about 0°C. a precipitate appears. The precipitate is separated from the liquid portion by filtration and then dissolved in and recrystallized from petroleum ether. The yellow solid is found to be soluble in diethyl ether and acetone, to be insoluble in water, and to have a melting point of about 89° to 91°C. and is identified by infrared and elemental analysis as meta-trifluoromethyl-1-thiooxaniloyl chloride, S-oxide

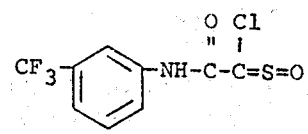

Calculated for $C_9H_5ClF_3NO_2S$: C, 38.11; H, 1.78; N, 4.94 Found: C, 38.38; H, 1.64; N, 4.84.

EXAMPLE 3

To a suitable reaction vessel equipped with an agitator is charged approximately 50 ml. of dichloromethane. Approximately 2.5 g., about 0.01 moles, of 2,2-dichloro-2(chlorothio)-para-acetotoluidide is added to and dissolved in the dichloromethane. Approximately 50 ml. of a saturated solution of sodium bicarbonate in water is then added. The reaction mass is stirred for about 1 hour at ambient room temperature, about 23°C. The mass is allowed to separate into two layers. The aqueous layer is removed in a separatory funnel. The remaining organic layer is dried over magnesium sulfate. The dichloromethane is removed from the organic layer by vacuum distillation leaving an orange solid. The solid is washed with diethyl ether, then dissolved in and recrystallized from petroleum ether. The orange solid is found to have a melting point of about 95° to 98°C., to be soluble in acetone and diethyl ether, and to be insoluble in water and is identified by nuclear magnetic resonance, infrared and elemental analysis as para-methyl-1-thiooxaniloyl chloride, S-oxide

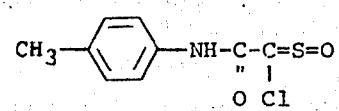

Calculated for $C_9H_8ClNO_2S$: C, 47.06; H, 3.51; N, 6.10 Found: C, 47.27; H, 3.50; N, 5.95.

EXAMPLE 4

To a suitable reaction vessel equipped with an agitator is charged approximately 50 ml. of dichloromethane. Approximately 10.2 g., about 0.03 moles, of meta-bromo-2,2-dichloro-2-(chlorothio)acetanilide is dissolved therein. Approximately 10 g., about 0.13 moles, of sodium bicarbonate is dissolved in about 50 ml. of water. This solution is then added. Thereafter the mass is stirred for about 1 hour at ambient room temperature, about 23°C. The mass is then allowed to separate into two layers. The aqueous layer is removed in a separatory funnel. The remaining organic layer is dried over magnesium sulfate. The dichloromethane is removed from the organic layer by vacuum distillation leaving a residual oil. The oil is partially dissolved in 100 ml. of petroleum ether. Upon cooling to about 10°C. a precipitate appears. The precipitate is separated from the liquid portion by filtration and then dissolved in and recrystallized from petroleum ether. The yellow solid is found to have a melting point of about 110 to 111°C., to be soluble in acetone, chloroform, ethanol, diethyl ether, and dimethylformamide, and to be insoluble in water, and is indentified by infrared and elemental analysis as meta-bromo-1-thiooxaniloyl chloride, S-oxide

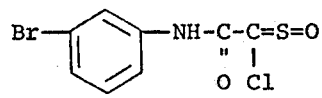

Calculated for $C_8H_5BrClNO_2S$: C, 32.62; H, 1.71; N, 4.76 Found: C, 32.66; H, 1.48; N, 4.53.

EXAMPLE 5

To a suitable reaction vessel equipped with an agitator is charged approximately 50 ml. of dichloromethane. Approximately 1.8 g., about 0.006 moles, of 2,2-dichloro-2-(chlorothio)para-methoxyacetanilide is added to and dissovled in the dichloromethane. Approximately 1.8 g., about 0.02 moles, of sodium bicarbonate is dissolved in about 50 ml. of water and then added. The reaction mass is stirred for about 1 hour at ambient room temperature, about 23°C. The mass is allowed to separate into two layers. The aqueous layer is removed in a separatory funnel. The remaining organic layer is dried over magnesium sulfate. The dichloromethane is removed from the organic layer by vacuum distillation leaving a residual solid. The red solid is washed with diethyl ether. The deep red solid is found to have a melting point of about 134° to 137°C., to be soluble in acetone, and to be insoluble in water and is identified by infrared and elemental analysis as para-methoxy-1-thiooxaniloyl chloride, S-oxide

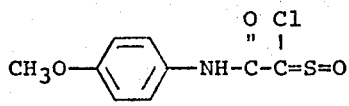

Calculated for $C_9H_8ClNO_3S$: C, 44.00; H, 3.28; N, 5.70 Found: C, 43.81; H, 3.22; N, 5.53.

EXAMPLE 6

To a suitable reaction vessel equipped with an agitator is charged about 200 ml. of dichloromethane. Approximately 20 g., about 0.066 moles, of 2,2-dichloro-2-(chlorothio)-2',6'-dimethylacetanilide is added and dissolved in the dichloromethane. The solution becomes homogeneous. Approximately 10 g., about 0.13 moles, of sodium bicarbonate is dissolved in about 200 ml. of water. This solution is then added. The mass is stirred for about 1 hour at ambient room temperature, about 23°C. The mass is allowed to separate into two layers. The aqueous layer is removed in a separatory funnel. The remaining organic layer is dried over magnesium sulfate. The dichloromethane is removed from the organic layer by vacuum distillation leaving a residual oil. The oil is dissolved in 100 ml. of hot petroleum ether. Upon cooling to about 0°C. a precipitate appears. The precipitate is separated from the liquid portion by filtration and then dissolved in and recrystalized from and then washed with petroleum ether. The tan solid is found to be soluble in diethyl ether, acetone, chloroform, and ethyl acetate, to be insoluble in water, and to have a melting point of about 101° to 109°C. and is identified by infrared and elemental analysis as 2',6'-dimethyl-1-thiooxaniloyl chloride, S-oxide

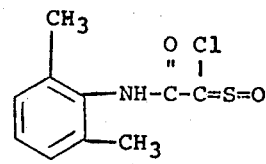

Calculated for $C_{10}H_{10}ClNO_2S$: C, 49.28; H, 4.14; N, 5.75 Found: C, 49.44; H, 4.25; N, 5.67.

EXAMPLE 7

To a suitable reaction vessel equipped with an agitator is charged approximately 50 ml. of dichloromethane. Approximately 30 g., about 0.088 moles, of 2,2-dichloro-2-(chlorothio)-6'-tert.-butyl-o-acetotoluidide is added to and dissolved in the dichloromethane. Approximately 30 g., about 0.4 moles, of sodium bicarbonate is dissolved in about 50 ml. of water. This solution is then added. The reaction mass is stirred for about 1 hour at ambient room temperature, about 23°C. The mass is allowed to separate into two layers. The aqueous layer is removed in a separatory funnel. The remaining organic layer is dried over magnesium sulfate. The dichloromethane is removed from the organic layer by vacuum distillation leaving a residual semi-solid. This residue is triturated with about 50 ml. of diethyl ether. The precipitate which forms is separated from the liquid portion by filtration. The white solid is found to have a melting point of about 168° to 169°C. and is identified by infrared and elemental analysis as 2'-tert.-butyl-6'-methyl-1-thiooxaniloyl choloride, S-oxide

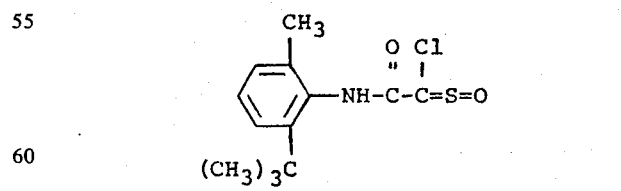

Calculated for $C_{13}H_{16}ClNO_2S$: C, 54.63; H, 5.64; N, 4.90 Found: C, 54.54; H, 5.64; N, 4.58.

EXAMPLE 8

To a suitable reaction vessel equipped with an agitator is charged approximately 50 ml. of dichloromethane. Approximately 5 g., about 0.02 moles, of 2,2'-dichloro-2-(chlrothio)propionanilide is added to and dissolved in the dichloromethane. Approximately 5 g., about 0.07 moles, of sodium bicarbonate is dissolved in about 50 ml. of water. This solution is then added. The reaction mass is stirred for about 1 hour at ambient room temperature, about 23°C. The mass is allowed to separate into two layers. The aqueous layer is removed in a separatory funnel. The remaining orgaic layer is dried over magnesium sulfate. The dichloromethane is removed from the organic layer by vacuum distillation leaving a residual semi-solid. The semi-solid is washed with diethyl ether and then dissolved in and recrystallized from diethyl ether. The yellow solid is found to have a melting point of about 103° to 105°C., to be soluble in acetone, and to be insoluble in water and is identified by infrared and elemental analysis as 2'-chloro-2-thiopyruvanilide, S-oxide

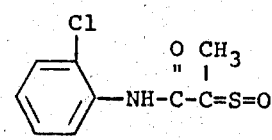

Calculated for $C_9H_8ClNO_2S$: C, 47.06; H, 3.51; N, 6.10
Found: C, 47.02; H, 3.68; N, 6.04.

EXAMPLES 9 THROUGH 27

The procedure of Example 1 is followed except that, in place of about 8 g. of 2,2,4'-trichloro-2-(chlorothio)-acetanilide, an approximately equimolecular amount of the compound of Column A is charged and the product of Column B is obtained:

| Example | A | B |
|---|---|---|
| 9 | 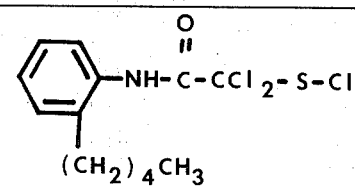 | 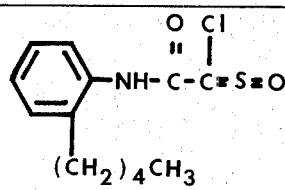 |
| 10 | 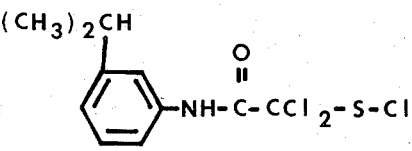 | 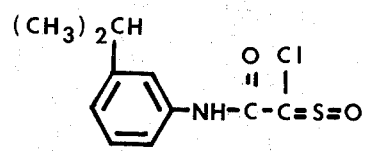 |
| 11 | 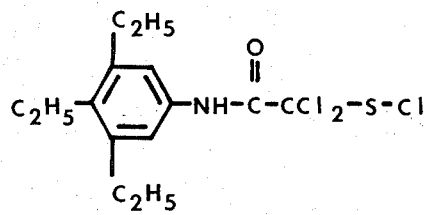 | 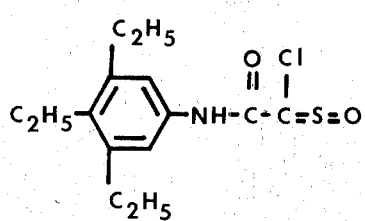 |
| 12 | 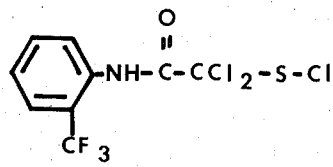 | 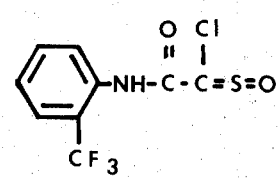 |
| 13 | 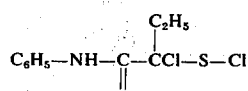 | 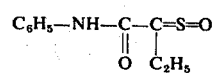 |
| 14 | 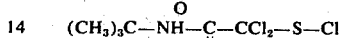 | $(CH_3)_3C-N-C-C=S=O$ <br> H  O  Cl |
| 15 | 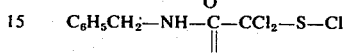 | $C_6H_5CH_2-NH-C-C=S=O$ <br>  O  Cl |
| 16 | 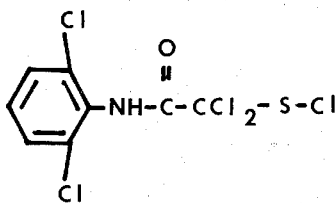 | 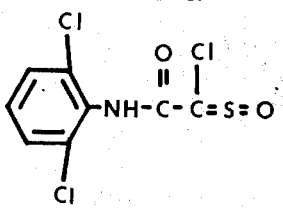 |

-continued
| Example | A | B |
|---|---|---|
| 17 | 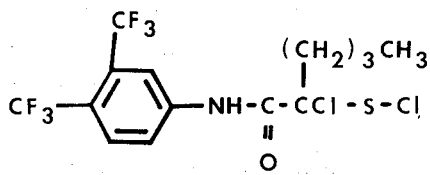 | 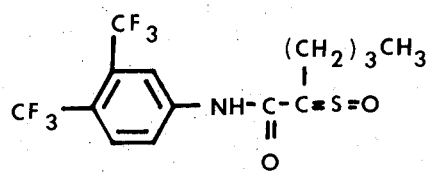 |
| 18 | 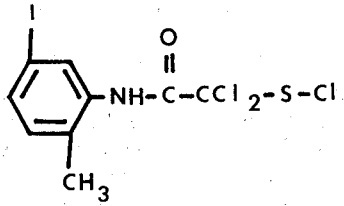 | 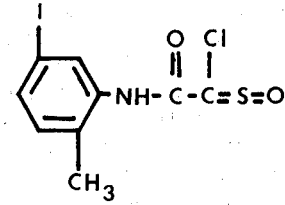 |
| 19 | 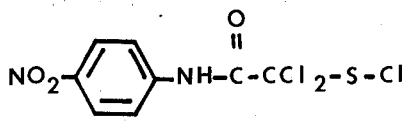 | 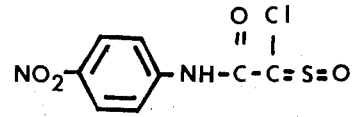 |
| 20 | 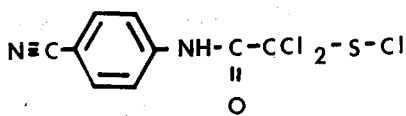 | 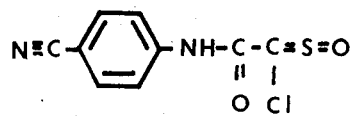 |
| 21 | 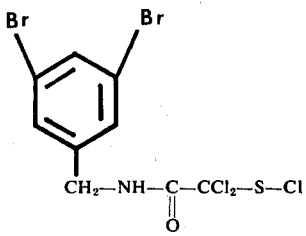 | 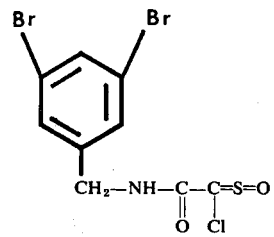 |
| 22 | 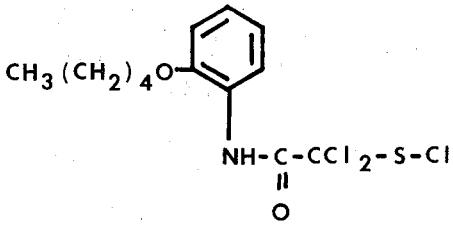 | 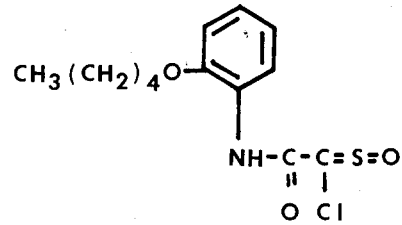 |
| 23 | 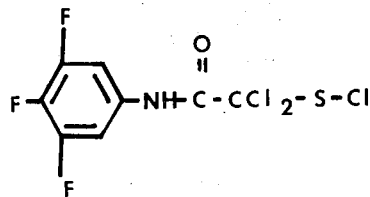 | 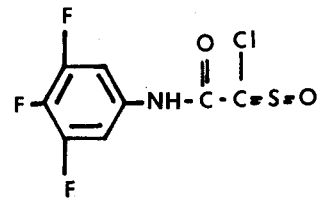 |
| 24 | 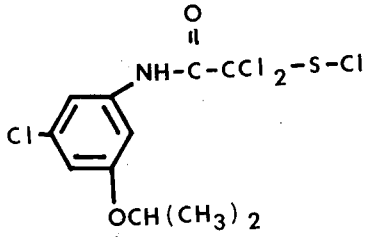 | 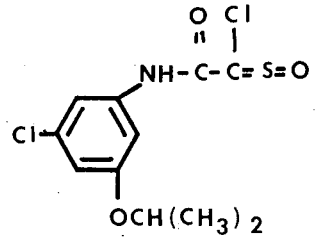 |
| 25 | 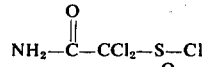 | 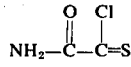 |
| 26 | 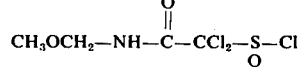 | 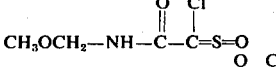 |
| 27 | 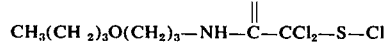 | 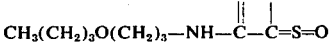 |

EXAMPLE 28

To a suitable reaction vessel equipped with an agitator is charged about 100 ml. of dichloromethane. Approximately 14 g., about 0.068 moles, of N,N-diisopropylcarbamoyl thioformyl chloride is added and dissolved in the dichloromethane. Approximately 13.7 g., about 0.06 moles, of meta-chloroperbenzoic acid is dissolved in about 100 ml. of dichloromethane. This solution is added slowly. The mass is stirred for about 1 hour. A precipitate which forms during the period of stirring is removed from the liquid portion of the reaction mass by filtration. The dichloromethane is removed by vacuum distillation leaving a residual oil. The oil is dissolved in 100 ml. of pentane. Upon cooling to about 0°C. a precipitate appears. The precipitate is separated from the liquid portion by filtration and then dissolved in dichloromethane. The solution is extracted with a cold dilute aqueous sodium bicarbonate solution, the dichloromethane is removed by vacuum distillation and the remaining oil is dissolved in and recrystallized from pentane. The white solid is found to have a melting point of about 47° to 51°C. and is identified by nuclear magnetic resonance, infrared and elemental analysis as N,N-diisopropyl-1-thiooxamoyl chloride, S-oxide

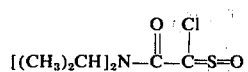

Calculated for $C_8H_{14}ClNO_2S$: C, 42.95; H, 6.31; N, 6.26 Found: C, 43.00; H, 5.99; N, 6.26

EXAMPLE 29

To a suitable reaction vessel equipped with an agitator is charged about 100 ml. of dichloromethane. Approximately 8.6 g., about 0.036 moles, of N-phenyl-N-isopropylcarbamoyl thioformyl chloride is added to and dissolved in the dichloromethane. Approximately 7 g., about 0.035 moles, of meta-chloroperbenzoic acid is dissolved in about 100 ml. of dichloromethane. This solution is then added. The reaction mass is stirred for about ½ hour at ambient room temperature, about 23°C. a precipitate appears. The reaction mass color turns from red to pale yellow. Slight warming of the mass is noted. The solid precipitate is removed from the mass by filtration. The dichloromethane is removed from the remaining liquid by vacuum distillation leaving a residual oil. The oil is partially dissolved in 100 ml. of petroleum ether. The remaining solid is removed by filtration and discarded. Upon cooling to about 0°C. a precipitate appears. The precipitate is separated from the liquid portion by filtration and then dissolved in pentane. The solution is filtered and then cooled to 0°C. A precipitate appears and is separated from the pentane by filtration. The solid is dissolved in dichloromethane, this solution is extracted with a cold dilute aqueous solution of sodium bicarbonate, and the dichloromethane is removed by vacuum distillation. The residue is dissolved in and recrystallized from pentane three times. The white solid is found to have a melting point of about 48° to 55°C., to be soluble in acetone, heptane, chloroform, diethyl ether, ethanol, ethyl acetate and dimethylformamide, and to be insoluble in water, and is identified by nuclear magnetic resonance, mass spectrometer, infrared and elemental analysis as N-phenyl-N-isopropyl-1-thiooxamoyl chloride, S-oxide

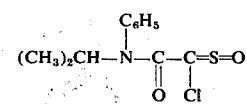

Calculated for $C_{11}H_{12}ClNO_2S$: C, 51.26; H, 4.69 Found: C, 51.26; H, 4.63

The wide melting point range apparently indicates a mixture of stereo-isomers.

EXAMPLES 30 THROUGH 43

The procedure of Example 28 is followed except that, in place of about 14 g. of N,N-diisopropylcarbamoyl thioformyl chloride, an approximately equimolecular amount of the compound of Column A is charged and the product of Column B is obtained:

| Example | A | B |
|---|---|---|
| 30 | 2,6-dimethylphenyl, N(CH₂OCH₃)-C(=O)-CCl=S | 2,6-dimethylphenyl, N(CH₂OCH₃)-C(=O)-C(Cl)=S=O |
| 31 | 2-methylphenyl, N(C₂H₅)-C(=O)-CCl=S | 2-methylphenyl, N(C₂H₅)-C(=O)-C(Cl)=S=O |
| 32 | (CH₂)₄N-C(=O)-CCl=S | (CH₂)₄N-C(=O)-C(Cl)=S=O |

| Example | A | B |
|---|---|---|
| 33 | 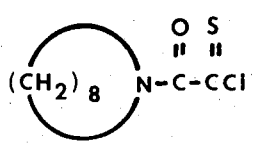 | 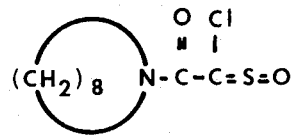 |
| 34 | 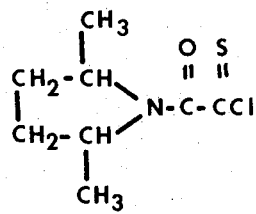 | 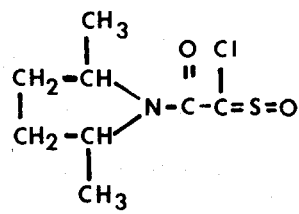 |
| 35 | 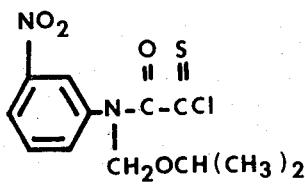 | 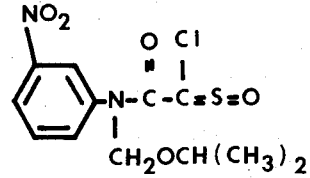 |
| 36 | 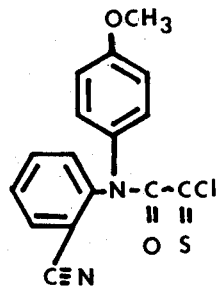 | 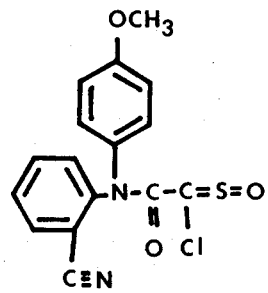 |
| 37 | 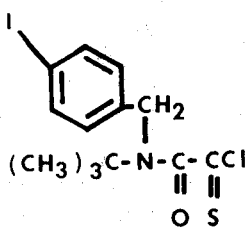 | 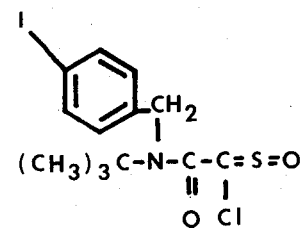 |
| 38 | 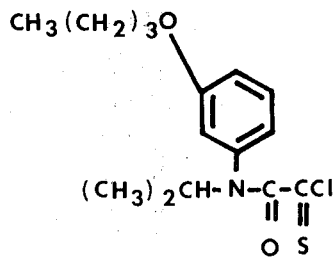 | 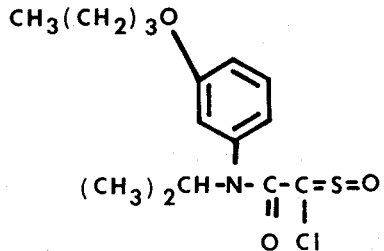 |
| 39 | 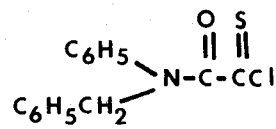 | 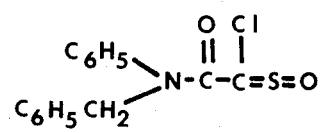 |

| Example | A | B |
|---|---|---|
| 40 | 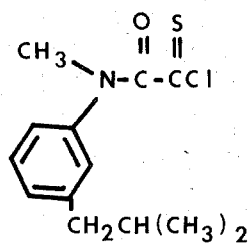 | 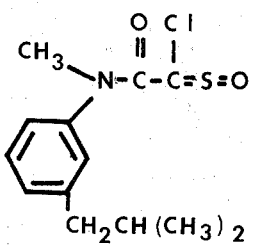 |
| 41 | 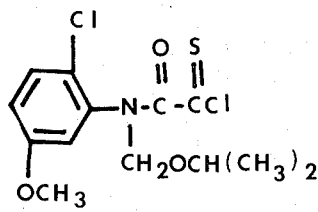 | 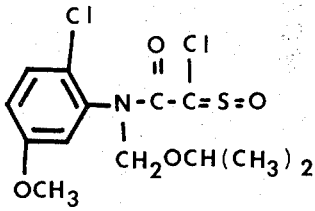 |
| 42 | 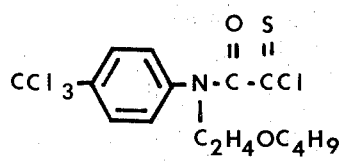 | 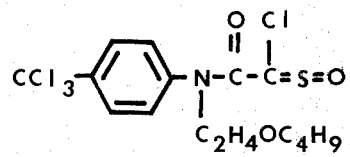 |
| 43 | 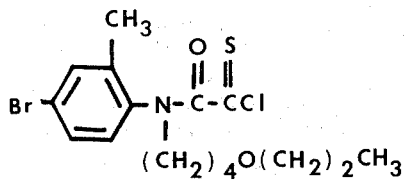 | 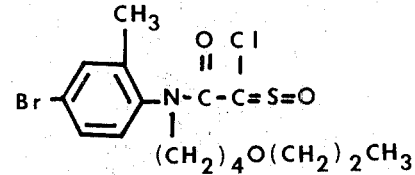 |

EXAMPLE 44

Contact herbicidal activity of representative substituted carbamoyl sulfines of this invention is determined by the following procedure:

The compound to be tested is applied in spray form to plants of a given age of several grasses and broadleaf species. After the plants are the desired age, each aluminum pan of plants is sprayed with a given volume of a 0.2% concentration solution of the candidate chemical, corresponding to a rate of approximately 4 lbs. per acre. This solution is prepared from an aliquot of a 2% solution of the candidate compound in acetone, a known amount of cyclohexanone-emulsifying agent mix, and sufficient water to make up to volume. The emulsifying agent is a mixture comprising 35 wt. percent butylamine dodecylbenzene sulfonate and 65 wt. percent of a tall oil-ethylene oxide condensate having about 6 moles of ethylene oxide per mole of tall oil. The injuries to the plants are then observed approximately 14 days later and the results are recorded.

Contact herbicidal activity of the compound prepared in Example 3 is observed against lambsquarter. Contact herbicidal activity of the compound prepared in Example 5 is observed against morning glory. Contact herbicidal activity of the compound prepared in Example 7 is observed against morning glory, lambsquarter and barnyard grass.

EXAMPLE 45

Pre-emergent herbicidal activity of representative substituted carbamoyl sulfines of this invention is determined by the following procedure:

A good grade of top soil is placed in aluminum pans and compacted to a depth of 3/8 to ½ inch from the top of the pan. A pre-determined number of seeds of each of several plant species are placed on top of the soil in the pans. The seeds are covered with soil and the pans leveled. The hericidal composition is applied by spraying the surface of the top layer of soil with a solution containing a sufficient amount of active ingredient to obtain a rate of application of 5 lbs. per acre. The pans are then placed on a sand bench in the greenhouse and watered from below as needed. The plants are observed at the end of approximately 14 days and the results recorded.

Pre-emergent activity of the compounds prepared in Examples 1 and 2 is observed against Canada thistle and lambsquarter. Pre-emergent activity of the compound prepared in Example 3 is observed against Canada thistle, cocklebur, velvet leaf, morning glory, lambsquarter and downy brome. Pre-emergent activity of the compound prepared in Example 5 is observed against barnyard grass. Pre-emergent activity of the compound prepared in Example 6 is observed against nutsedge and barnyard grass. Pre-emergent activity of the compound prepared in Example 7 is observed against barnyard grass, downy brome, Johnson grass, quackgrass, nutsedge, lambsquarter, morning glory, velvet leaf, cocklebur and Canada thistle. Pre-emergent activity of the compound prepared in Example 8 is observed against nutsedge, Johnson grass, and barnyard grass. Pre-emergent activity pre-emergent the compound prepared in Example 29 is observed against morning glory and barnyard grass.

While the illustrative embodiments of the invention have been described hereinbefore with particularity, it will be understood that various other modifications will be apparent to and can readily be made by those skilled in the art without departing from the scope and spirit of the invention. Accordingly, it is not intended that the scope of the claims appended hereto be limited to the examples and description set forth herein but rather the claims be construed as encompassing all the features of patentable novelty which reside in the present invention including all features which would be treated as equivalents thereof by those skilled in the art to which the invention pertains.

What is claimed is:

1. A substituted carbamoyl sulfine of the formula

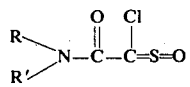

wherein R and R' are each independently selected from hydrogen, lower alkyl, alkoxyalkyl of from 2 through 8 carbons, benzyl, phenyl, substituted phenyl wherein the ring substituents thereof total from 1 through 3 same or different substituents selected from the group of substituents consisting of lower alkyl, lower alkoxy, halo, nitro, and trihalomethyl, provided that the number of nitro substituents be from 0 through 2, and substituted benzyl wherein the substituents are on the phenyl ring and are as defined for substituted phenyl.

2. A compound of claim 1 wherein R is hydrogen.
3. A compound of claim 1 wherein R' is substituted phenyl.
4. A compound of claim 3 wherein the ring substituents are halo.
5. A compound of claim 4 wherein the halo is chlorine.
6. The compound of claim 5 wherein R' is para-chlorophenyl.
7. A compound of claim 4 wherein the halo is bromine.
8. The compound of claim 7 wherein R' is meta-bromophenyl.
9. A compound of claim 3 wherein the ring substituents are trihalomethyl.
10. The compound of claim 9 wherein R' is metatrifluoromethylphenyl.
11. A compound of claim 3 wherein the ring substituents are lower alkoxy.
12. The compound of claim 11 wherein R' is paramethoxyphenyl.
13. A compound of claim 3 wherein the ring substituents are lower alkyl.
14. The compound of claim 13 wherein R' is paramethyl phenyl.
15. The compound of claim 13 wherein R' is 2,6-dimethylphenyl.
16. The compound of claim 13 wherein R' is 2-tert.-butyl-6-methylphenyl.
17. A compound of claim 1 wherein R' is substituted benzyl.
18. A compound of claim 1 wherein R' is lower alkyl.
19. A compound of claim 1 wherein R' is alkoxyalkyl of from 2 through 8 carbons.
20. A compound of claim 1 wherein R is lower alkyl.
21. A compound of claim 20 wherein R' is substituted phenyl.
22. A compond of claim 20 wherein R' is phenyl.
23. The compound of claim 22 wherein R is isopropyl.
24. A compound of claim 20 wherein R' is lower alkyl.
25. The compound of claim 24 wherein R and R' are both isopropyl.
26. A compound of claim 1 wherein R is substituted phenyl.
27. A compound of claim 26 wherein R' is alkoxyalkyl of 2 through 8 carbons.
28. A method for the preparation of substituted carbamoyl sulfines of the formula

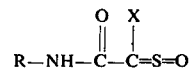

wherein R is selected from hydrogen, lower alkyl, alkoxyalkyl of from 2 through 8 carbons, benzyl, phenyl, substituted phenyl wherein the ring substituents thereof total from 1 through 3 same or different substituents selected from the group of substituents consisting of lower alkyl, lower alkoxy, halo, nitro, and trihalomethyl, provided that the number of nitro substituents be from 0 through 2, and substituted benzyl wherein the substituents are on the phenyl ring and are as defined for substituted phenyl, and X is chloro or lower alkyl, which comprises reacting at temperatures above the freezing point of the system to about 50°C about one molecular proportion of a chloromethane sulfenyl chloride of the formula

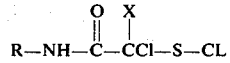

wherein R and X have the aforementioned significance and about two equivalent proportions of an aqueous base selected from the group consisting of alkali metal carbonates and bicarbonates and alkali metal hydroxides of up to 0.1 molar strength.

29. Method according to claim 28 wherein said reaction occurs at temperatures within the range of from about 0°–30°C and said base is aqueous sodium bicarbonate.

30. Method according to claim 28 wherein said aqueous base is 0.1 molar solution of an alkali metal hydroxide.

* * * * *